(12) United States Patent
Lim et al.

(10) Patent No.: US 6,450,682 B1
(45) Date of Patent: Sep. 17, 2002

(54) METHOD AND APPARATUS FOR PREDICTING THE END OF LIFE OF A GAS SCRUBBER

(75) Inventors: Kye-Jin Lim; Gwon Sagong, both of Seoul (KR); Daniel K. Weber, Atascadero, CA (US)

(73) Assignee: C&M Inc., Seoul (KR)

( * ) Notice: Subject to any disclaimer, the term of this patent is extended or adjusted under 35 U.S.C. 154(b) by 0 days.

(21) Appl. No.: 09/479,496

(22) Filed: Jan. 7, 2000

(51) Int. Cl.[7] .............................................. G01N 25/00
(52) U.S. Cl. ........................................ 374/45; 374/137
(58) Field of Search .......................... 374/45, 137, 179, 374/166, 102; 96/420; 95/25; 436/147; 422/51

(56) References Cited

U.S. PATENT DOCUMENTS

| | | |
|---|---|---|
| 2,016,928 A | 10/1935 | Lombardi |
| 3,311,305 A | 3/1967 | Crownover |
| 3,434,522 A | 3/1969 | Laurenty |
| 3,465,504 A | 9/1969 | Oropeza et al. |
| 3,721,608 A | 3/1973 | Saller et al. |
| 3,815,332 A | 6/1974 | Bobrowsky et al. |
| 4,221,574 A | 9/1980 | Loggins, Jr. et al. |
| 4,241,021 A | 12/1980 | Skrzec |
| 4,350,662 A | 9/1982 | Dowgul et al. |
| 4,487,139 A | 12/1984 | Warner |
| 5,209,766 A | 5/1993 | Reither |
| 5,762,692 A | 6/1998 | Dumas et al. |
| 5,869,323 A | * 2/1999 | Horn .......................... 435/262 |
| 5,873,929 A | 2/1999 | Andreani et al. |
| 5,939,582 A | * 8/1999 | Dassel et al. ................ 562/413 |
| 6,068,686 A | 5/2000 | Sorensen et al. |
| 6,106,596 A | 8/2000 | Haramoto et al. |
| 6,126,913 A | * 10/2000 | Martin et al. ............. 423/245.3 |
| 6,136,144 A | * 10/2000 | Martin et al. ................. 162/14 |
| 6,158,147 A | 12/2000 | Smith et al. |

* cited by examiner

*Primary Examiner*—Diego Gutierrez
*Assistant Examiner*—Yaritza Guadalupe
(74) *Attorney, Agent, or Firm*—Oppenheimer Wolff & Donnelly LLP

(57) ABSTRACT

A method and system for predicting the end of life of a packed resin or dry chemical bed in a gas scrubber including providing a plurality of thermocouples spacedly disposed in the packed bed, the thermocouples being operatively coupled to a processor, monitoring the motion of an exothermic wavefront through the packed resin or dry chemical bed by periodically sampling the thermocouples and computing a time at which the exothermic wavefront will have traversed the packed resin or dry chemical bed, the computed time being the end of life of the packed resin or dry chemical bed.

22 Claims, 5 Drawing Sheets

CM1

| SPECIES | REACTION |
|---|---|
| $BCl_3$ | $BCl_3 + 3MOH \rightarrow 3MCl + B(OH)_3$ |
| $BF_3$ | $BF_3 + 3MOH \rightarrow 3MF + B(OH)_3$ |
| $Cl_2$ | $Cl_2 + 2MOH \rightarrow 2MCl + H_2O + 1/2O_2$ |
| $F_2$ | $F_2 + 2MOH \rightarrow 2MF + H_2O + 1/2O_2$ |
| $SiF_4$ | $SiF_4 + 6MOH \rightarrow M_2SiO_3 + 4MF + 3H_2O$ |
| $WF_6$ | $WF_6 + 6MOH \rightarrow M_2WO_4 + 6MF + 4H_2O$ |

| GAS TYPE | SPECIES | REACTION |
|---|---|---|
| Halogen-containing waste gas | BCl$_3$ | 2BCl$_3$ + 3M(OH)$_2$ -> 3MCl$_2$ + B$_2$O$_3$ + 3H$_2$O |
| | | CBl$_3$ + 3MO(OH) -> 3MOCl + B(OH)$_3$ |
| | | 2BCl$_3$ + M$_2$O$_3$ -> 2MCl$_3$ + 2B$_2$O$_3$ |
| | | BCl$_3$ + 3MOH -> 3MCl + B(OH)$_3$ |
| | | BCl$_3$ + 3H$_2$O -> B(OH)$_3$ + 3HCl + 3/2O$_2$ |
| | BF$_3$ | BF$_3$ + 3MOH -> 3MF + B(OH)$_3$ |
| | | BF$_3$ + 3H$_2$O -> B(OH)$_3$ + 3HF + 3/2O$_2$ |
| | Cl$_2$ | Cl$_2$ + M(OH)$_2$ -> MCl$_2$ + H$_2$O + 1/2O$_2$ |
| | | Cl$_2$ + 2MO(OH) -> 2MOCl + H$_2$O + 1/2O$_2$ |
| | | 3Cl$_2$ + M$_2$O$_3$ -> 2MCl$_3$ + 3/2O$_3$ |
| | | Cl$_2$ + 2MOH -> 2MCl + H$_2$O + 1/2O$_2$ |
| | | Cl$_2$ + H$_2$O -> 2HCl + 1/2O$_2$ |
| | HBr | 2HBr + M(OH)$_2$ -> MBr$_2$ + 2H$_2$O |
| | | 3HBr + MO(OH) -> MBr$_3$ + H$_2$O + 1/2O$_2$ |
| | | 3HBr + M$_2$O$_3$ -> MBr$_3$ + H$_2$O |
| | HCl | 2HCl + M(OH)$_2$ -> MCl$_2$ + 2H$_2$O |
| | | 3HCl + MO(OH) -> MCl$_3$ + H$_2$O + 1/2O$_2$ |
| | | 3HCl + M$_2$O$_3$ -> MCl$_3$ + H$_2$O |
| | HF | 2HF + M(OH)$_2$ -> MF$_2$ + 2H$_2$O |
| | | 3HF + MO(OH) -> MF$_3$ + H$_2$O + 1/2O$_2$ |
| | | 3HF + M$_2$O$_3$ -> MF$_3$ + H$_2$O |
| | F$_2$ | F$_2$ + 2MOH -> 2MF + H$_2$O + 1/2O$_2$ |
| | | F$_2$ + H$_2$O -> 2HF + 1/2O$_2$ |
| | SiCl$_3$H | 2SiCl$_3$H + 3M(OH)$_2$ -> 3MCl$_2$ + 2/3SiO$_2$ + 4H$_2$O |
| | SiCl$_4$ | SiCl$_4$ + 2M(OH)$_2$ -> 2MCl$_2$ + SiO$_2$ + H$_2$O |
| | SiHCl$_3$ | 2SiHCl$_3$ + 3M(OH)$_2$ -> 3MCl$_2$ + 2/3SiO$_2$ + 4H$_2$O |
| | SiH$_2$Cl$_2$ | SiH$_2$Cl$_2$ + M(OH)$_2$ -> MCl$_2$ + SiO$_2$ + 2H$_2$ |
| | SiF$_4$ | SiF$_4$ + 2M(OH)$_2$ -> 2MF$_2$ + SiO$_2$ + 2H$_2$O |
| | | SiF$_4$ + 6MOH -> M$_2$SiO$_3$ + 4MF + 3H$_2$O |
| | WF$_6$ | WF$_6$ + 3M(OH)$_2$ -> 3MF$_2$ + WO$_3$ + 3H$_2$O |
| | | WF$_6$ + 6MOH -> M$_2$WO$_4$ + 6MF + 4H$_2$O |
| Perfluoro-compounds (PFC) | ClF$_3$ | 2ClF$_3$ + 4M(OH)$_2$ -> 3MF$_2$ + MCl$_2$ + 4H$_2$O + 2O$_2$ |
| | NF$_3$ | 2NF$_3$ + 3M(OH)$_2$ -> 3MF$_2$ + 3H$_2$O + N$_2$ + 3/2O$_2$ |
| | SF$_6$ | SF$_6$ + 2M(OH)$_2$ -> 2MF$_2$ + SiO$_2$ + 2H$_2$O |

FIG. 3

|    | TC1  | TC2  | TC3  |
|----|------|------|------|
| T1 | 50°C | 25°C | 20°C |
| T2 | 25°C | 50°C | 25°C |
| T3 | 20°C | 25°C | 50°C |
FIG. 4
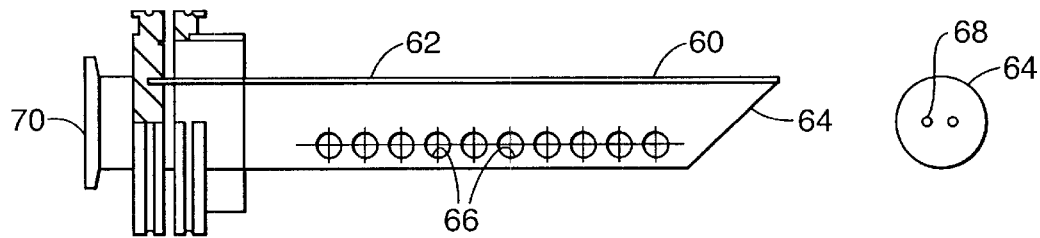
FIG. 5       FIG. 6
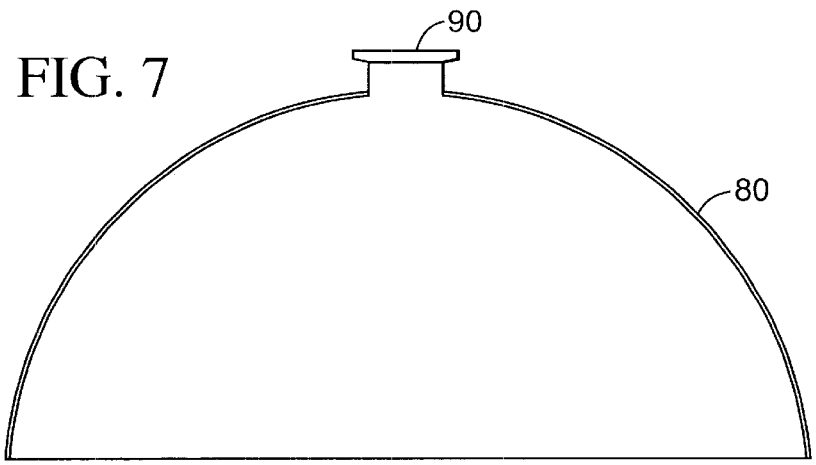
FIG. 7

METHOD AND APPARATUS FOR PREDICTING THE END OF LIFE OF A GAS SCRUBBER

CROSS REFERENCE TO RELATED APPLICATIONS

This application is related to co-pending patent application Nos. 09/479,428, 09/479,497, and 09/479,502, all filed Jan. 7, 2000.

FIELD OF THE INVENTION

The present disclosure relates to gas purifiers and more particularly to packed resin or dry chemical bed gas scrubber systems for the treatment of effluent gases produced in semiconductor manufacturing.

BACKGROUND OF THE INVENTION

In the fabrication of semiconductor devices toxic and corrosive gases, including halogenated species, are used in both etch and deposition processes. After use in a process chamber, the effluent gas stream must be treated before being exhausted into the environment. Several scrubbing devices attachable to an exhaust of the process chamber are known in the art.

Known scrubbing devices consist generally of three types; those which burn the flammable components of the effluent gas stream, those which decompose water soluble components of the effluent stream in a wetting method and those which adsorb toxic components using adsorbents to chemically and physically decompose the toxic components. Stand-alone scrubbers of the adsorptive type must be periodically replaced as the adsorbent material is used in adsorbing the toxic components and as the adsorbent becomes deactivated with the by-products of reactions between the adsorbent and toxic compounds.

In addressing the problem of determining when to replace the stand-alone scrubber, prior art devices generally employ two techniques. A first technique includes tracking a change in the weight of the scrubber. Such a technique is utilized, for example, in the Ebara Corporation Model No. 3-0/6-0-/9-0. This technique provides a method by which the end of life of the adsorbent material is indicated but does not accurately provide a method for predicting the end of life of the adsorbent material, and is not particularly accurate as changes in the weight of the scrubber attributable to other causes are not taken into consideration.

A second technique includes monitoring a color change in the adsorbent resin wherein the color change is observable through a sight glass. Such a technique is utilized, for example, in the Japan Pionics Corporation Model No. PCF-60B-CT. As in the case of the first technique, the second technique provides a method by which the end of life of the adsorbent material is indicated but does not provide a method of predicting the end of life of the adsorbent material. Further, a subjective element is introduced by the person viewing the color change which introduces human error into the end of life determination.

There therefore exists a need for a stand-alone scrubber system of the packed resin or dry chemical bed type which provides for the accurate, objective and automatic prediction of the end of life of the adsorbent material.

SUMMARY OF THE INVENTION

A packed resin or dry chemical bed scrubber system and method for the treatment of effluent gases produced in semiconductor manufacturing is disclosed. In a preferred embodiment, the system includes a packed resin or dry chemical bed having a first resin or dry chemical layer packed between two layers of a second resin or dry chemical. A bottom screen and a top screen are provided for supporting the packed resin or dry chemical bed within a canister and to provide a substantially laminar flow of the effluent gases through the packed resin or dry chemical bed. An end of life detection and prediction system includes a plurality of spaced thermocouples positioned within the first resin or dry chemical layer and operatively coupled to a processor for monitoring the movement of an exothermal wavefront at each position and for predicting an end of life condition of the first resin or dry chemical layer.

The packed resin or dry chemical canister includes a bottom plenum and a top plenum disposed at opposite ends of the packed resin or dry chemical bed. A dispersion nozzle is disposed within the bottom plenum at an inlet formed in communication with the bottom plenum. The dispersion nozzle includes a plurality of apertures for directing the flow of the effluent gases from the semiconductor fabrication tool into the bottom plenum. The apertures are sized and configured to eliminate back pressure into the semiconductor fabrication tool and to disperse the effluent gases into the bottom plenum for subsequent laminar flow through the packed resin or dry chemical bed.

A top portion of the canister includes an outlet in communication with the top plenum. The top portion further includes a dome of arcuate cross section. This configuration is optimized to provide for substantially laminar flow of the effluent gases through the packed resin or dry chemical bed.

DESCRIPTION OF THE DRAWINGS

The present disclosure will be better understood when consideration is given to the following detailed description. Such description makes reference to the annexed drawings, wherein:

FIG. 2 is a table showing representative reactions of the first resin or dry chemical material;

FIG. 3 is a table showing representative reactions of the second resin or dry chemical material;

FIG. 4 is a table showing exemplary temperature readings as the exothermic wavefront traverses the packed resin or dry chemical bed;

FIG. 5 is a partial cross sectional view of the dispersion nozzle;

FIG. 6 is an end view of the end portion of the dispersion nozzle;

FIG. 7 is a side elevation view of the dome;

DETAILED DESCRIPTION

Figure 1:
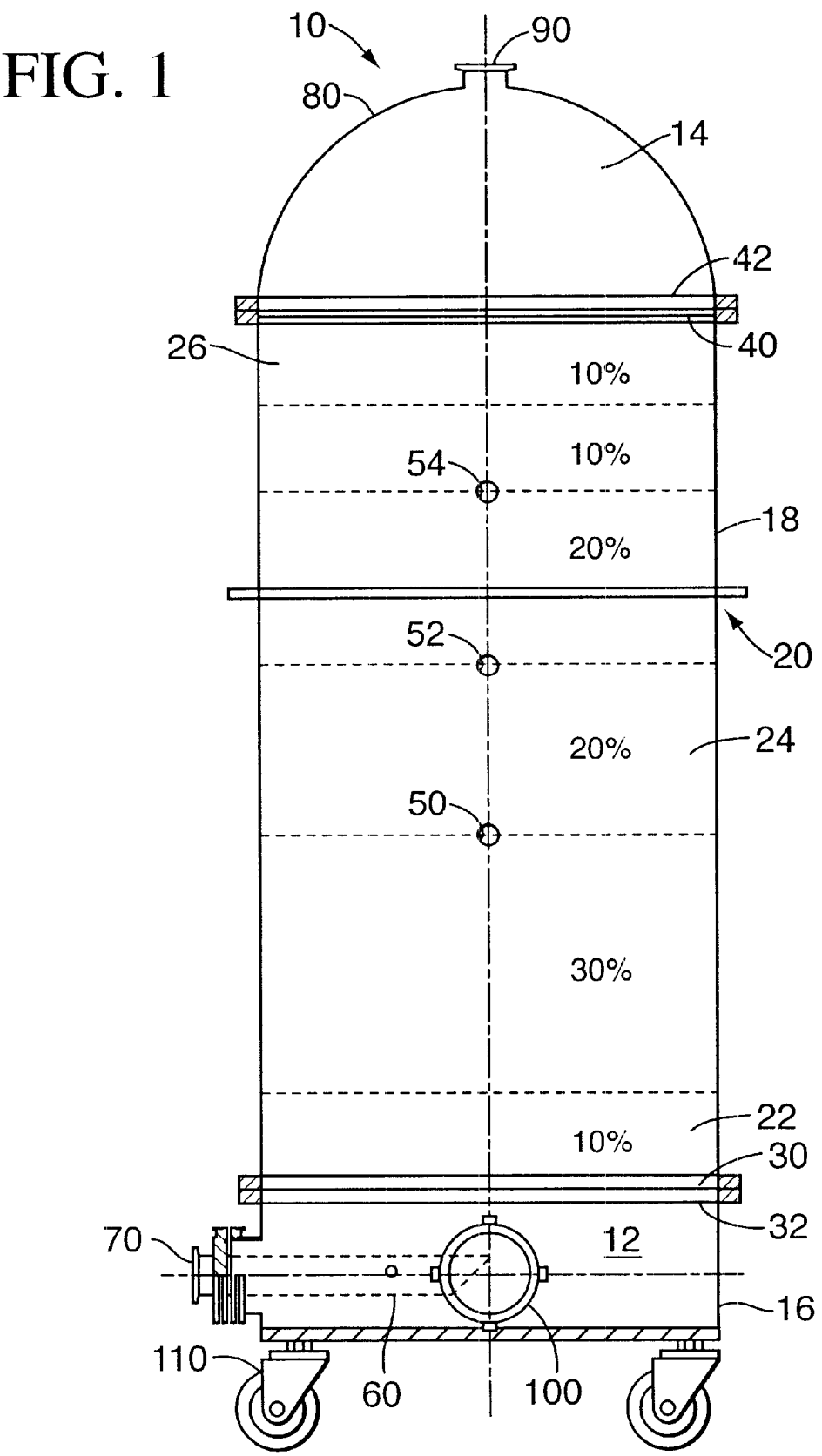
FIG. 1 is a side elevation view of a canister in accordance with a disclosed embodiment.

An end of life prediction system disclosed herein uses the uniform movement of an exothermal wavefront through a resin or dry chemical bed typically maintained at ambient temperature (e.g. about 25° C.). To achieve this uniform movement, a packed bed canister, generally designated 10 in FIG. 1, includes the packed resin or dry chemical bed generally designated 20 and components and features that urge an upward laminar flow of effluent gases from a semiconductor fabrication tool through the canister 10. As will be appreciated by those skilled in the art, a number of resins or dry chemicals may be used in the disclosed scrubber system depending upon the application and other factors. The described resins or dry chemicals should therefore be considered illustrative and not limiting as to the types of resins or dry chemicals used.

The packed resin or dry chemical bed 20 is disposed between a first screen 30 and a second screen 40 the design of which will be further described hereinbelow. The packed resin or dry chemical bed 20 includes a first cylindrical layer of a second resin or dry chemical material and comprises approximately 10% of the volume of the packed resin or dry chemical bed 20. The second resin or dry chemical material is of a type which preconditions halogen species in the effluent gases produced in a semiconductor fabrication tool (not shown). The second resin or dry chemical is an acid neutralizing composition consisting of metal hydroxides on an extruded, pelletized clay substrate. The second resin or dry chemical material is available from C&M Inc., #308 Sungwoo Plaza, 1047-6 Hogye-Dong, Dongan-Gu, Anyang City, Kyngki-Do, Korea under the tradename CM2. A table of representative reactions in the first layer 22 is shown in FIG. 3.

A first cylindrical layer 24 of a first resin or dry chemical material comprises approximately 80% of the volume of the packed resin or dry chemical bed 20 and is disposed between the first layer 22 of the second resin or dry chemical material and a second cylindrical layer 26 of the second resin or dry chemical material. The first resin or dry chemical material is of a type which reacts with halogenated species and perfluoro compounds as shown in the table in FIG. 2. The first resin or dry chemical material is a composition consisting of nitrate compounds on a steam-activated extruded carbon substrate. The first resin or dry chemical material is available from C&M Inc. under the tradename CM1. The second layer 26 of the second resin or dry chemical material is operable to react with, and has a high capacity for, Cl⁻ species as the effluent gases exit the packed resin or dry chemical bed 20.

A preferred embodiment of an end of life monitor and predictor system includes a plurality of thermocouples embedded in the first layer 24 of the first resin or dry chemical. Each of the plurality of thermocouples is embedded in the first layer 24 at an edge portion thereof (not shown). The thermocouples are preferably of pt 100 ohm type. Preferably, a first thermocouple 50 is embedded in the first layer 24 of the first resin or dry chemical at a first position approximately $\frac{1}{10}$ of the distance from a bottom surface thereof adjacent the bottom screen 30 and top surface thereof adjacent the top screen 40. A second thermocouple 52 is preferably embedded in the first layer 24 of the first resin or dry chemical at a second position $\frac{5}{10}$ of the distance from the bottom screen 30 to the top screen 40. A third thermocouple 54 is preferably embedded in the first layer 24 of the first resin or dry chemical at a third position $\frac{8}{10}$ of the distance from the bottom screen 30 to the top screen 40. In this configuration the distance between the first position and the second position is the same as the distance between the second position and the third position. Furthermore, the distance between the third position and an interface between the first layer 24 of the first resin or dry chemical and the second layer 26 of the second resin or dry chemical is half the distance between the second position and the third position.

Thermocouples 50, 52 and 54 are operably coupled to a processor (not shown) operable to monitor the motion of an exothermic wavefront which moves through the packed resin or dry chemical bed 20 as effluent gases flow through the canister 10. The wavefront is kept as uniform as possible by urging an upward laminar flow of the gases through the system. A plurality of well type connectors (not shown) are formed in the canister 10 through which cables (not shown) connect the thermocouples 50, 52, and 54 to the processor. Those skilled in the art will appreciate that the processor may include a microprocessor, a programmable logic controller, a discreet circuit or any other device or circuit for providing an output representative of the thermocouple output. The processor is operable to monitor the motion of the exothermic wavefront by sampling the thermocouples 50, 52, and 54 and recording the temperature at each of the first, second and third positions over time. By way of example and not limitation, and making reference to the table shown in FIG. 4, a method of predicting the end of life of the first layer 24 of the first resin or dry chemical will now be described. The actual temperatures are simplified for the purposes of the example.

In FIG. 4, at a beginning time T1, thermocouple 50 indicates that the temperature at the first position is 50° C., thermocouple 52 indicates that the temperature at the second position is 25° C. and thermocouple 54 indicates that the temperature at the third position is 20° C. At a time T2, thermocouple 50 indicates that the temperature at the first position is 25° C., thermocouple 52 indicates that the temperature at the second position is 50° C. and thermocouple 54 indicates that the temperature at the third position is 25° C. At a time T3, thermocouple 50 indicates that the temperature at the first position is 20° C., thermocouple 52 indicates that the temperature at the second position is 25° C. and thermocouple 54 indicates that the temperature at the third position is 50° C. One skilled in the art will appreciate that the elevated temperatures (50° C.) indicate the positioning of the exothermic wavefront at the respective first, second or third positions within the first layer 24 of the first resin or dry chemical. The processor is operable to compute a time $\Delta T21=T2-T1$ and a time $\Delta T32=T3-T2$. It is expected. that $\Delta T21$ will be approximately equal to $\Delta T32$. The end of life of the first layer 24 of the first resin or dry chemical is then computed as $(\Delta T21)/2$ since the exothermic wavefront can be expected to travel through the remaining portion of the first layer 24 of the first resin or dry chemical in half the time.

In order to urge a uniform movement of the exothermic wavefront through the packed resin or dry chemical bed 20, laminar flow of the effluent gases from the semiconductor fabrication tool through the packed resin or dry chemical bed 20 is provided. Laminar flow is established through the packed resin or dry chemical bed 20 by providing a dispersion nozzle 60 in communication with a canister inlet port 70 which disperses the effluent gases in a canister bottom plenum 12, first and second screens 30 and 40 which further disperse and distribute the effluent gases within the canister 10 and a dome 80 of semicircular cross section which encloses a canister top plenum 14.

With reference to FIG. 5, the dispersion nozzle 60 is shown including an elongated cylindrical portion 62 extending from the canister inlet port 70 and terminating at a downwardly angled portion 64. A plurality of apertures 66 are spacedly formed along the elongated portion 62 on opposite sides of the elongated portion 62 (opposite side apertures not shown) and disposed below an equatorial plane of the elongated portion 62 to direct incoming effluent gases to the bottom of the bottom plenum 12 (FIG. 1).

As shown in FIG. 6, a pair of apertures 68 are shown formed in the downwardly angled portion 64. By virtue of the orientation of the downwardly angled portion 64, effluent gases flowing through the apertures 68 are directed to the bottom of the bottom plenum 12.

The combined areas of the apertures 66 and apertures 68 is greater than the area of a cross section of the elongated portion 62 to reduce the chance that back pressure will develop forcing the effluent gases back into the semiconductor fabrication tool.

With reference to FIG. 7, the dome 80 includes a semi-circular cross sectional profile. The dome 80 further includes an outlet port 90 to which is generally attached a fan or vacuum source (not shown) to draw the effluent gases through the canister 10 for processing. The design of the dome 80 reduces "dead spaces" in the packed resin or dry chemical bed 20 in an area proximate the second layer 26 and promotes laminar flow of the effluent gases through the canister 10.

Figure 8:
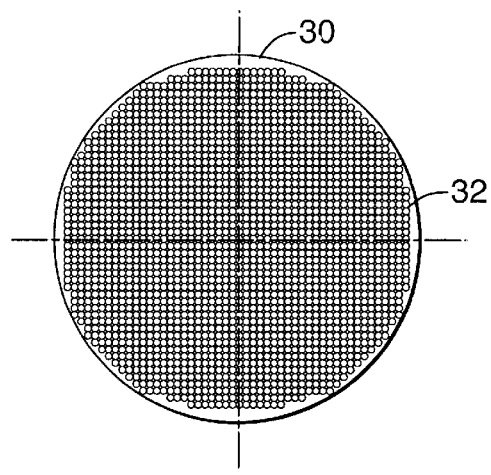
FIG. 8 is a top plan view of a screen.

As seen in FIG. 1, first and second screens 30 and 40 respectively are provided for enclosing the packed resin or dry chemical bed 20 within the canister 10. As shown in FIG. 8, the first screen 30 includes a circular member having a preferred thickness of 10 mm and a plurality of apertures 32 formed therethrough. The apertures 32 are sized and configured to retain the packed resign bed 20 above the first screen 30 and are preferably less than 3 mm in diameter, the second resin or dry chemical material having a diameter greater than 3 mm. As shown in FIG. 1, the first screen 30 provides support for the first layer 22 of second resin or dry chemical material and further provides a boundary between the packed resin or dry chemical layer 20 and the bottom plenum 12. As will be appreciated by those skilled in the art, the apertures 32 further provide for the dispersal of the effluent gases dispersed by the dispersal nozzle 60 and as such provide for laminar flow through the packed resin or dry chemical bed 20.

The second screen 40 is of identical size and configuration as the first screen 30 and is disposed at a top of the second layer 26 of the second resin or dry chemical. The second screen 40 further provides a bottom of the top plenum 14. The second screen additionally provides for laminar flow through the packed resin or dry chemical bed 20.

As shown in FIG. 1, the canister 10 is comprised of three sections. A first section 16 provides an enclosure for the bottom plenum 12. The first section 16 is preferably joined to a second section 18 which provides an enclosure for the packed resin or dry chemical bed 20 at a first flange 32. To the second section 18 is joined the dome 80 at a second flange 42. As shown the first and second screens 30 and 40 are disposed at the first and second flanges 32 and 42 respectively.

Figure 10:
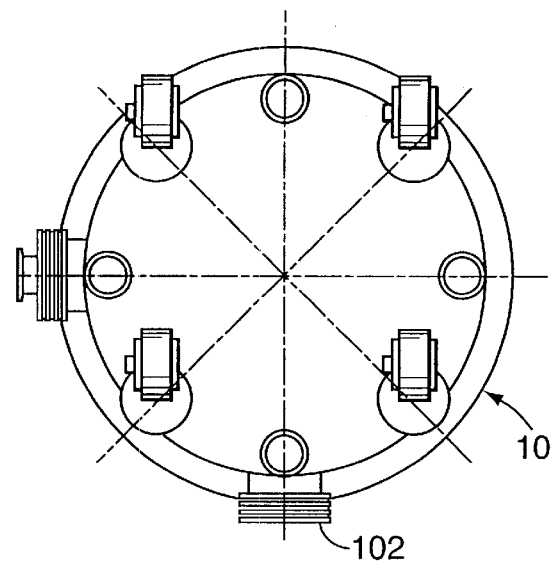
FIG. 10 is a bottom plan view of the canister.
Figure 9:
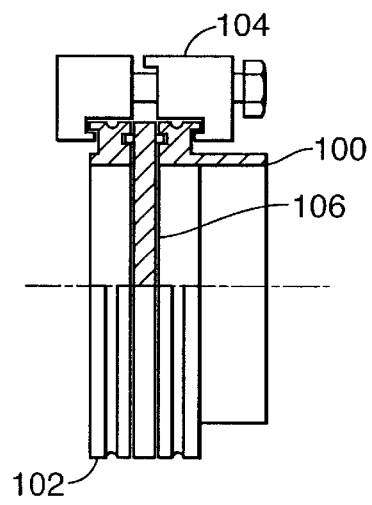
FIG. 9 is a partial cross sectional view of the sight glass.

A common problem encountered in packed resin or dry chemical bed scrubbers involves the clogging of the device by particles created in the reaction of the effluent gases with the resin or dry chemical material. A preferred embodiment provides for a sight glass 100 as shown in FIGS. 1, 9 and 10. The sight glass 100 is positioned at a bottom portion of the canister 10 and oriented to provide a view of the dispersion nozzle 60. A flange 102 formed on an outside portion of the canister 10 includes a claw clamp 104 for securing a removable glass member 106 from the flange 102.

Figure 11:
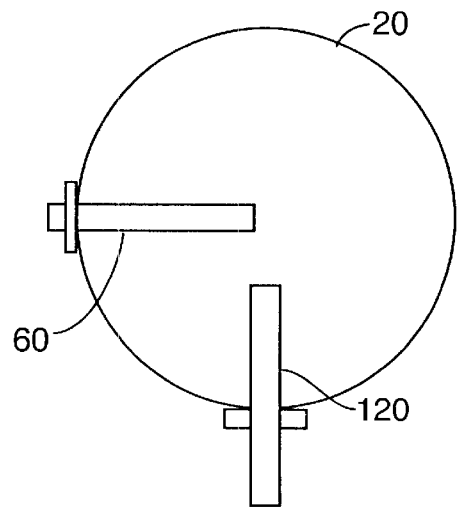
FIG. 11 is a schematic view showing an in-situ cleaning of the bottom plenum.

Visual inspection of the bottom plenum 12, dispersion nozzle 60 and bottom screen 30 is made possible by the positioning of the sight glass 100. In the case where a buildup of particles is observed in any of the bottom plenum 12, the dispersion nozzle 60 or the bottom screen 30, the glass member 106 may be removed in-situ and these components accessed as with a vacuum cleaning device 120 (FIG. 11) for removal of the accumulated particles. Removal of particles from the dispersion nozzle 60 prevents the build-up of back pressure in the semiconductor fabrication tool and prevents particles from reaching the fabrication tool. As previously described, the bottom screen 30 functions to ensure laminar flow through the packed resin or dry chemical bed 20 and thus the removal of particles therefrom is important in maintaining such laminar flow.

In use, the effluent gases of the semiconductor fabrication tool enter the canister 10 at the inlet 70. A pressure differential between the top plenum 14 and the bottom plenum 12 is created by an exhaust or vacuum source connected to the outlet 90. Preferably a pressure differential of 5 mm of water is established between the top plenum 14 and the bottom plenum 12, the top plenum being about 100 mm of water below atmospheric pressure and the bottom plenum 12 being about 95 mm of water below atmospheric pressure. The effluent gases are dispersed by the dispersion nozzle 60 and directed to the bottom of the bottom plenum 12. The effluent gases are next drawn through the bottom screen 30 and through the packed resin or dry chemical bed 20. Laminar flow through the packed resin or dry chemical bed 20 provides for a uniform exothermic wavefront which travels through the packed resin or dry chemical bed 20 as the effluent gases react with the constituents of the packed resin or dry chemical bed 20. The thermocouples 50, 52 and 54 coupled to the processor detect and monitor the movement of the exothermic wavefront and the processor is operable to predict the end of life of the packed resin or dry chemical bed 20.

In a preferred embodiment, the canister 10 is formed from stainless steel and is 1370 mm high and has an internal diameter of 444 mm. The dome 80 has a radius of 222 mm and is joined to a bottom of the canister at a position corresponding to the position of the second screen 40. The packed resin or dry chemical bed 20 has a depth of 876 mm and the bottom plenum 12 has a depth of 151.5 mm. The first and second screens 30 and 40 have a diameter of 440 mm. As shown in FIG. 1, the canister 10 further includes a plurality of casters 110 disposed at a bottom surface thereof for providing mobility to the canister 10.

The dispersion nozzle 60 is preferably 260 mm long and 38.1 mm in diameter, the angled portion 64 being angled in a downward direction and extending from an end of the dispersion nozzle and terminating at a position 38 mm from the end of the dispersion nozzle.

While various embodiments have been described above, it should be understood that they have been presented by way of example only, and not limitation. Thus, the breadth and scope of an embodiment of the disclosed invention should not be limited by any of the above described exemplary embodiments, but should be defined only in accordance with the following claims and their equivalents.

What is claimed is:

1. A method for predicting the end of life of a packed resin or dry chemical bed in a gas scrubber comprising:
   monitoring the motion of an exothermic wavefront through the bed; and
   computing a time at which the exothermic wavefront will have traversed the bed, the computed time being the end of life of the bed.

2. A method as recited in claim 1 wherein the monitoring step further comprises providing a plurality of thermocouples spacedly disposed in the bed, the thermocouples being operatively coupled to a processor.

3. A method as recited in claim 2 wherein the packed bed further comprises a layer of a first material intermediate first and second layers of a second material and wherein the thermocouples are disposed in the layer of the first material.

4. A method as recited in claim 3 wherein the computed time is the end of life of the layer of the first material.

5. A method as recited in claim 3 wherein the layer of the first material further comprises a bottom surface and a top surface, and wherein a first thermocouple is disposed at a first position spaced from the bottom surface, a second thermocouple is disposed at a second position spaced from the first thermocouple by a first distance in a direction oriented toward the top surface and a third thermocouple is disposed at a third position spaced from the second thermocouple by the first distance in the direction oriented toward the top surface, the third thermocouple being spaced from a top surface by a second distance, the second distance being half of the first distance.

6. A method as recited in claim 5 wherein the computed time is half a second computed time determined by monitoring the motion of the exothermic wavefront from the second position to the third position.

7. A method as recited in claim 5 wherein the computed time is twice a third computed time determined by monitoring the motion of the exothermic wavefront from the first position to the second position plus a fourth computed time equal to half the third computed time.

8. A method as recited in claim 1 wherein the bed is disposed in a canister between a bottom plenum and a top plenum, the bottom plenum having an inlet and the top plenum having an outlet.

9. A method as recited in claim 8 wherein the bed is bounded by a first screen adjacent the bottom plenum and a second screen adjacent the top plenum.

10. A method as recited in claim 8 wherein the canister is cylindrical and the top plenum has a substantially semicircular cross section.

11. A method as recited in claim 8 wherein the bottom plenum further comprises a dispersion nozzle disposed therein, the dispersion nozzle being in communication with the inlet.

12. An apparatus for predicting the end of life of a bed in a gas scrubber comprising:

a plurality of thermocouples spacedly disposed in the bed, the thermocouples being operatively coupled to a processor, the processor operable to monitor the motion of an exothermic wavefront through the bed by periodically sampling the thermocouples and computing a time at which the exothermic wavefront will have traversed the bed, the computed time being the end of life of the bed.

13. An apparatus as recited in claim 12 wherein the bed further comprises a layer of a first material intermediate first and second layers of a second material and wherein the thermocouples are disposed in the layer of the first material.

14. An apparatus as recited in claim 13 wherein the computed time is the end of life of the layer of the first material.

15. An apparatus as recited in claim 13 wherein the layer of the first material further comprises a bottom surface and a top surface, and wherein a first thermocouple is disposed at a first position spaced from the bottom surface, a second thermocouple is disposed at a second position spaced from the first thermocouple by a first distance in a direction oriented toward the top surface and a third thermocouple is disposed at a third position spaced from the second thermocouple by the first distance in the direction oriented toward the top surface, the third thermocouple being spaced from a top surface by a second distance, the second distance being half of the first distance.

16. An apparatus as recited in claim 15 wherein the computed time is half a second computed time determined by monitoring the motion of the exothermic wavefront from the second position to the third position.

17. An apparatus as recited in claim 15 wherein the computed time is twice a third computed time determined by monitoring the motion of the exothermic wavefront from the first position to the second position plus a fourth computed time equal to half the third computed time.

18. An apparatus as recited in claim 12 wherein the bed is disposed in a canister between a bottom plenum and a top plenum, the bottom plenum having an inlet and the top plenum having an outlet.

19. An apparatus as recited in claim 18 wherein the bed is bounded by a first screen adjacent the bottom plenum and a second screen adjacent the top plenum.

20. An apparatus as recited in claim 18 wherein the canister is cylindrical and the top plenum has a substantially semicircular cross section.

21. An apparatus as recited in claim 18 wherein the bottom plenum further comprises a dispersion nozzle disposed therein, the dispersion nozzle being in communication with the inlet.

22. A method for predicting the end of life of a packed resin or dry chemical bed in a gas scrubber comprising:

urging a laminar flow of gases through the bed;

monitoring the motion of an exothermic wavefront through the bed, the exothermic wavefront resulting from a reaction between the gases and the bed; and computing a time at which the exothermic wavefront will have traversed the bed, the computed time being the end of life of the bed.

* * * * *